United States Patent [19]

Takakarhu

[11] Patent Number: 5,180,558
[45] Date of Patent: Jan. 19, 1993

[54] METHOD AND APPARATUS FOR TAKING SAMPLES

[75] Inventor: Jouni Takakarhu, Helsinki, Finland

[73] Assignee: Neste OY, Finland

[21] Appl. No.: 707,463

[22] Filed: May 30, 1991

[30] Foreign Application Priority Data

Jun. 7, 1990 [FI] Finland ................... 902839

[51] Int. Cl.⁵ .................... C08F 2/00; C08G 85/00
[52] U.S. Cl. .................... 422/131; 422/119; 422/132; 526/59; 526/64
[58] Field of Search .............. 422/131, 132, 62, 119, 422/114; 436/85, 55; 73/863.86, 863.71; 526/59, 64

[56] References Cited

U.S. PATENT DOCUMENTS

| | | | |
|---|---|---|---|
| 3,257,363 | 6/1966 | Miller et al. | 526/59 |
| 3,293,000 | 12/1966 | Marwil | 526/64 |
| 3,427,138 | 2/1969 | Donnelly et al. | 422/131 |
| 3,429,186 | 2/1969 | Price et al. | 73/863.86 |
| 3,556,730 | 1/1971 | Mitacek | 436/85 |
| 3,950,136 | 4/1976 | Bellinga | 73/863.86 |

*Primary Examiner*—Robert J. Warden
*Assistant Examiner*—Krisanne M. Thornton
*Attorney, Agent, or Firm*—Steinberg & Raskin

[57] ABSTRACT

The invention relates to a method and an apparatus for continuously taking a sample from a discharge system of a polymerization reactor having a discontinuously opening discharge valve connecting the polymerization reactor to a product tube leading into a solid-constituent separation system. A sampling means having a closing valve of an on/off type is connected to the product tube. The closing valve closes for the period of a pressure wave occurring when the discharge valve opens, and opens after the pressure wave. A buffer container connected to an analyzer is provided with a sufficient volume to maintain the continuity of the sample flow when the closing valve is closed.

7 Claims, 1 Drawing Sheet

METHOD AND APPARATUS FOR TAKING SAMPLES

FIELD OF THE INVENTION

The invention relates to a method and an apparatus for continuously taking samples from a product flow comprising a pressurized suspension containing solid polymer particles, a diluent and monomers.

BACKGROUND OF THE INVENTION

Various methods for preparing solid semi-solid polymers from hydrocarbons, e.g. from 1-olefines have been developed.

In one such method olefines, such as ethylene, propene, butene or pentanes, are polymerized in the presence of catalysts in hydrocarbon diluents or the monomers themselves act as diluents. Reactants are then kept in a solution phase by maintaining a suitable pressure in the polymerization reactor. When the resultant polymer is insoluble or slightly soluble in said diluent, the polymer product is formed as particles and the product flow thus comprises a suspension formed by polymer particles, a diluent and monomers. This product flow is usually led into a polymer separation container, in which the solid substances as well as liquid and gaseous constituents are separated from each other.

One reactor type applied in such methods is a continuous tube reactor forming a loop, in which reactor the polymerization occurs in a turbulent flow circulating in a loop. The product containing the polymer, a diluent and monomer is taken from the loop reactor either continuously or more usually discontinuously via a discharge valve, and it is led to a separator, in which the polymer is separated by reducing the pressure.

For regulating the polymerization reaction, it is possible to take samples continuously or discontinuously from the product flow of the reactor. The normal way of taking a sample from the gas flow exiting from the polymer separation container and of analyzing this sample with various methods, e.g. by means of gas chromatography. Such an arrangement is described e.g. in U.S. Pat. No. 3,556,730.

In this known procedure the delay which is needed from the exiting of the product from the polymerization reactor to the initial moment of the analysis, is often considerably long and essential changes can occur meanwhile in the process. In other words, the sampling according to this patent is coupled directly to the reactor, so the sample represents the condition which prevailed in the reactor at the moment of taking the sample. The sample is thus not in all times representative. It would then be preferable that the analysis delay could be shortened.

OBJECTS AND SUMMARY OF THE INVENTION

An object of the present invention is to provide a method by means of which the time needed to obtain samples from a polymerization reactor as described above is substantially shortened.

This object and others are accomplished by the present invention, which relates to a method for continuously taking a sample from a product flow of a polymerization reactor, which product flow contains a polymer, a diluent and monomers and which exit from a polymerization reactor via a discontinuously opening discharge valve and a product tube into a solid-constituent separation container.

The sample is taken from the product tube via a closing valve of on/off type which closes for the period of a pressure wave occurring when a pressure wave from the reactor enters the product flow, i.e., when the discharge valve opens, and which closing valve opens after the pressure wave.

It has surprisingly been discovered that although the sample is taken directly from a suspension containing polymer particles, diluents and monomers, the inventive method provides a sample containing only few or no polymer particles.

In accordance with one embodiment of the invention, when using a substantially horizontally oriented product tube, said closing valve is located above the product tube, whereby the sample flow via the closing valve occurs from below upwards. This arrangement facilitates the fact that the polymer particles do not enter amount the sample.

In accordance with a preferred embodiment of the invention, the sample is led from the closing valve into a separate buffer container. Since the sample flow going to the analyzers must preferably be maintained constant, the closing of the closing valve would cause a break in the sample flow. By means of the buffer container, the analyzers obtain the sample also during the time when the closing valve is closed. The flow from the buffer container to the analyzer preferably occurs via a constant flow valve, which maintains flow to the analyzer constant.

The present invention is also related to an apparatus for continuously taking a sample from the discharge system of the polymerization reactor, which system contains a discontinuously opening discharge valve as well as a product tube leading to the solid constituent separation system and means for taking a sample from the product tube.

The sampling means in the present invention comprises a closing valve of the on/off type, which closes for the period of a pressure wave occurring when the discharge valve opens, and opens after the pressure wave, and in addition comprises a buffer container whose volume is preferably sufficient to maintain the continuity of the sample flow when the closing valve is closed.

In accordance with one embodiment of the inventive apparatus, the closing valve is located above the product tube. In accordance with a further embodiment of the inventive apparatus, the apparatus includes a constant flow valve, which maintains a constant flow from the buffer container to the analyzers.

BRIEF DESCRIPTION OF THE DRAWINGS

The inventive method and apparatus is next described with reference to the accompanying FIGS. 1 and 2.

DETAILED DESCRIPTION

Figure 1:
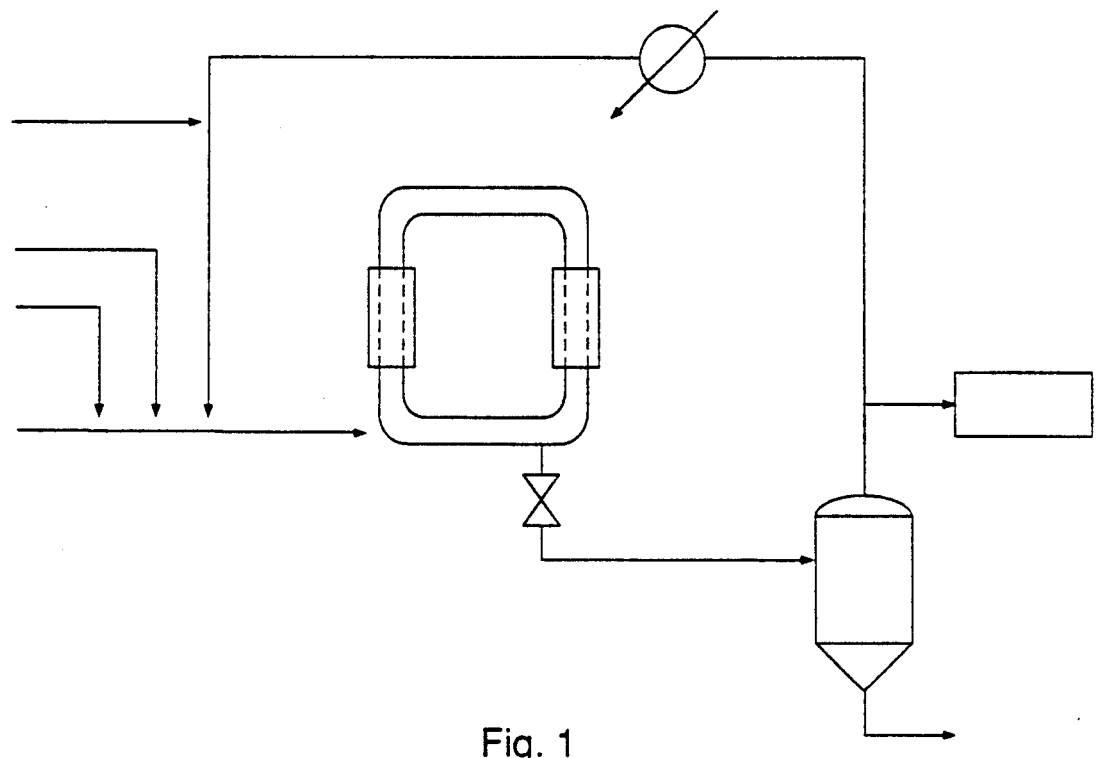
FIG. 1 is a schematic diagram of a conventional loop reactor system.

In FIG. 1, the reference number 10 relates to a polymerization apparatus, in which a monomer is led via a feeding line 11 from a line 12, a catalyst from a line 13 and a diluent from a line 14 to a loop reactor 15. In a line 16 of the reactor 15, a suspension formed by reactants and the resultant polymer is circulated at a high speed by means of a circulating apparatus (not shown), e.g. a pump or a propelling device. The temperature of the reactor 15 can be regulated by means of a heating/cooling sleeve 17.

The reactant feeding system described above is only illustrative, and reactants can thus be led into the reactor 15 in any manner desired together or separately.

The suspension of the polymer, the diluent and the monomer is removed from the reactor 15 via a valve 18. The valve opens discontinuously for a short period of time, e.g. at intervals of half a minute, and allows the product suspension to enter via a product tube 19 into a separation container 20.

In the separation container 20, owing to a pressure reduction, the diluent contained in the suspension is gasified, whereby the solid polymer product exits via a pipe 21 and the gaseous phase containing the diluent and the monomer exist via a pipe 22. The gaseous phase can be returned to the reactor 15 along a pipe 24 after a pressure increase occurring in a compressor 23.

From the pipe 22, it is possible to take a gas sample via a pipe 25 for an analyzer 26. Since the volume of the separator 20 is considerably large and since the product flow to the separator is discontinuous, a considerably long time is consumed for a proper mixing of the gas phase and a forming of a representative sample, which can even last for 15 minutes. A considerable analyzing delay is thus caused by this fact.

Figure 2:
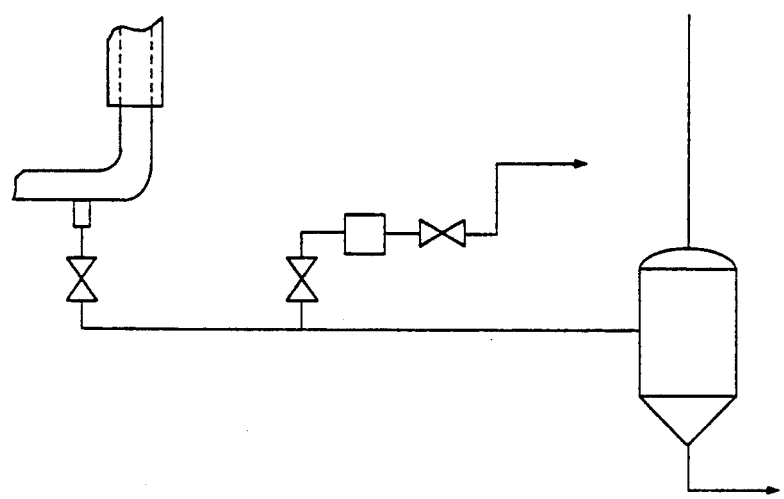
FIG. 2 is a schematic diagram of an apparatus according to the present invention.
Figure 1:
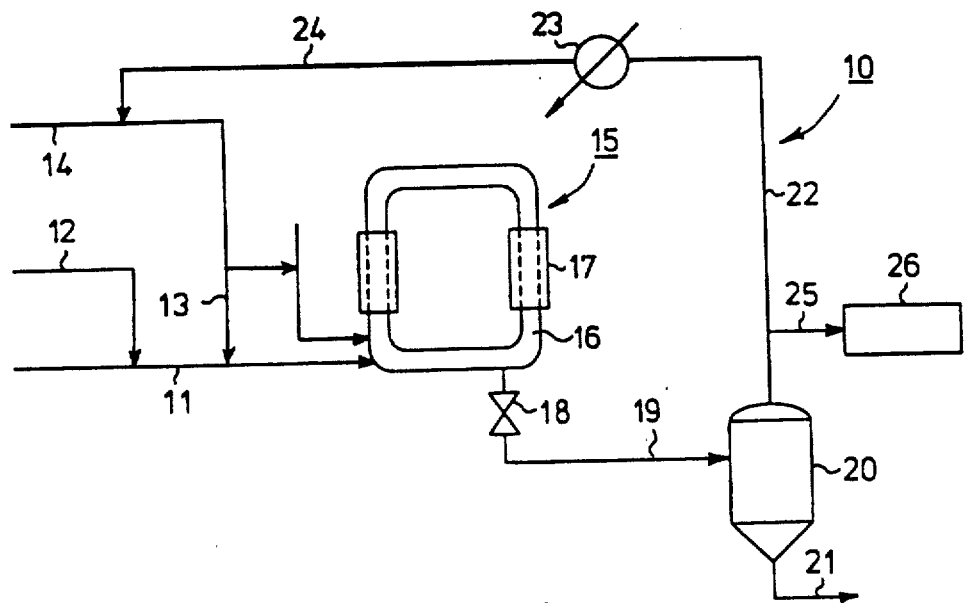
Figure 2:
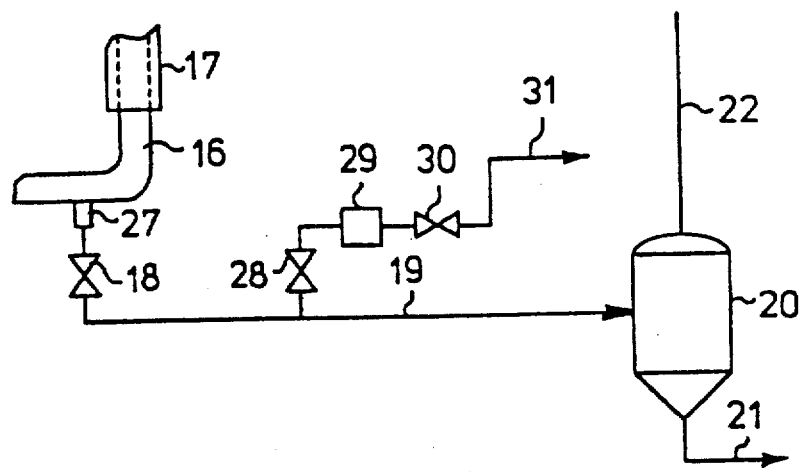

The inventive sampling system is shown in FIG. 2. The sample is taken from the reactor 15 via a block 27 and the discharge valve 18 relatively rapidly directly from the product tube 19 via a valve 28 via a constant flow valve 30 to a pipe 31 entering the analyzer.

When the discharge valve 18 opens, the pressure of the reactor 15 can enter directly into the product pipe 19, causing a considerable pressure wave. This pressure wave must not enter the analyzers, and because of this, a valve of on/off type is used as the valve 28, which closes, as the discharge valve opens for the period of the greatest pressure wave. The duration of the pressure wave is about 5 seconds. After the pressure wave, the valve 28 opens, allowing the sample to flow to the analyzer via the valve 30 and the pipe 31.

In order that the sample flow to the analyzer is continuous, a buffer container 29 is preferably arranged after the valve 28, the volume of which container is dimensioned such that it is sufficient to ensure that the flow via the pipe 31 is continuous, although the valve 28 is discontinuously closed.

EXAMPLE

The process delay caused by the analysis was about 10 minutes in the polymerization apparatus of FIG. 1, in which the sample was taken via the separation container, the volume of which is about 2 cubic meters.

When the sampling system was changed according to FIG. 2, the process delay caused by the analysis was reduced to 1 minute under otherwise similar conditions. The volume of the buffer container used was 1 liter.

Many other variations of the present invention would be obvious to one skilled in the art, and are contemplated to be within the scope of the appended claims.

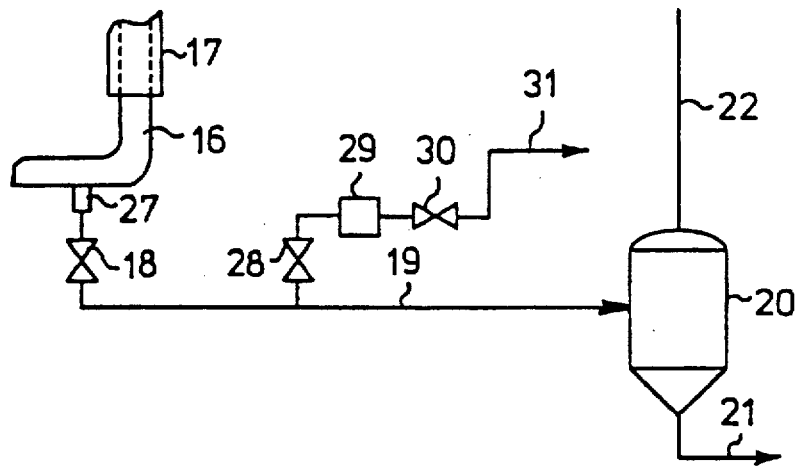

I claim:

1. A method for continuously taking a sample from a product flow removed from a polymerization reactor, which product flow comprises a polymer, a diluent and monomers and which exits from the polymerization reactor via a discontinuously opening discharge valve into a solid-constituent separation container, comprising the steps of
    taking the sample from a product tube containing product flow discharged from said polymerization reactor via an on/off type valve,
    arranging said on/off valve to be closed for a period of a pressure wave occurring when said discharge valve opens, and
    arranging said on/off valve to open after said pressure wave has ended.

2. A method according to claim 1 further comprising providing a substantially horizontally oriented product flow via a substantially horizontally oriented section of said product tube from said discharge valve, and arranging said on/off valve above said horizontally oriented product flow.

3. A method according to claim 1, further comprising directing said sample from said on/off valve to an analyzer via a buffer container whose volume is sufficient to maintain a sample flow when the on/off valve is closed.

4. An apparatus for continuously taking a sample from a discharge system of a polymerization reactor comprising
    a discontinuously opening discharge valve connected to a polymerization reactor,
    a product tube containing product flow from a polymerization reactor leading from said discharge valve into a solid-constituent separation system,
    an on/off valve connected to said product tube, said on/off valve closing for the period of a pressure wave occurring when the discharge valve opens and opening after the pressure wave has ended, such that product samples are taken from a product flow removed from said polymerization reactor,
    a buffer container connected at one end to said on/off valve and another end to analyzing means, said buffer container having a sufficient volume to maintain the continuity of a sample flow to said analyzing means when the on/off valve is closed.

5. An apparatus according to claim 4, wherein said product tube is substantially horizontally oriented and said on/off valve is arranged at about a 90° angle above said product tube.

6. An apparatus according to claim 4, further comprising a constant flow valve which maintains a constant flow of a sample from said buffer container to an analyzer.

7. An apparatus for continuously taking a sample from a discharge flow removed from a polymerization reactor comprising
    a polymerization reactor for producing a product comprising a polymer, a diluent and monomers,
    a discontinuously opening discharge valve connected to said polymerization reactor,
    a product tube leading from said discharge valve, said discharge valve opening for an interval of time to allow said product to enter said product tube, a solid-constituent separation container connected to said product tube for separating said product into constituent parts, a on/off valve connected to a substantially horizontally oriented section of said product tube and oriented above said section, said on/off valve connected to said product tube at a location between said discharge valve and said solid-constituent separation chamber, said on/off valve closing for the period of a pressure wave emanating from said polymerization reactor and occurring when said discharge valve opens and said on/off valve opening after the pressure wave has ended, such that product samples are taken from a product flow removed from said polymerization reactor, and
a buffer container connected at one end to said on/off valve and at another end to analyzing means, said buffer container having a sufficient volume to maintain the continuity of the sample flow to said analyzing means when the on/off valve is closed.

* * * * *

UNITED STATES PATENT AND TRADEMARK OFFICE
CERTIFICATE OF CORRECTION

PATENT NO. : 5,180,558

DATED : January 19, 1993

INVENTOR(S) : Takakarhu

It is certified that error appears in the above-indentified patent and that said Letters Patent is hereby corrected as shown below:

The title page showing the illustrative Figure should be deleted to be replaced with the attached title page.

The sheet of drawings consisting of Figs. 1 and 2, should be deleted to be replaced with the corrected Figs. 1 and 2, as shown on the attached page.

Signed and Sealed this

First Day of February, 1994

Attest:

BRUCE LEHMAN

Attesting Officer          Commissioner of Patents and Trademarks

United States Patent [19]

Takakarhu

[11] Patent Number: 5,180,558
[45] Date of Patent: Jan. 19, 1993

[54] METHOD AND APPARATUS FOR TAKING SAMPLES

[75] Inventor: Jouni Takakarhu, Helsinki, Finland
[73] Assignee: Neste OY, Finland
[21] Appl. No.: 707,463
[22] Filed: May 30, 1991

[30] Foreign Application Priority Data

Jun. 7, 1990 [FI] Finland .................. 902839

[51] Int. Cl.⁵ .................. C08F 2/00; C08G 85/00
[52] U.S. Cl. .................. 422/131; 422/119; 422/132; 526/59; 526/64
[58] Field of Search .................. 422/131, 132, 62, 119, 422/114; 436/85, 55; 73/863.86, 863.71; 526/59, 64

[56] References Cited

U.S. PATENT DOCUMENTS

| | | | |
|---|---|---|---|
| 3,257,363 | 6/1966 | Miller et al. | 526/59 |
| 3,293,000 | 12/1966 | Marwil | 526/64 |
| 3,427,138 | 2/1969 | Donnelly et al. | 422/131 |
| 3,429,186 | 2/1969 | Price et al. | 73/863.86 |
| 3,556,730 | 1/1971 | Mitacek | 436/85 |
| 3,950,136 | 4/1976 | Bellinga | 73/863.86 |

Primary Examiner—Robert J. Warden
Assistant Examiner—Krisanne M. Thornton
Attorney, Agent, or Firm—Steinberg & Raskin

[57] ABSTRACT

The invention relates to a method and an apparatus for continuously taking a sample from a discharge system of a polymerization reactor having a discontinuously opening discharge valve connecting the polymerization reactor to a product tube leading into a solid-constituent separation system. A sampling means having a closing valve of an on/off type is connected to the product tube. The closing valve closes for the period of a pressure wave occurring when the discharge valve opens, and opens after the pressure wave. A buffer container connected to an analyzer is provided with a sufficient volume to maintain the continuity of the sample flow when the closing valve is closed.

7 Claims, 1 Drawing Sheet